(12) United States Patent
Coudon

(10) Patent No.: US 6,628,195 B1
(45) Date of Patent: Sep. 30, 2003

(54) TACTILE STIMULATION DEVICE FOR USE BY A DEAF PERSON

(76) Inventor: Jean-Max Coudon, La Buchetterie, 6 Avenue Hildegarde, 49240 Avrille (FR)

( * ) Notice: Subject to any disclaimer, the term of this patent is extended or adjusted under 35 U.S.C. 154(b) by 0 days.

(21) Appl. No.: 09/706,692

(22) Filed: Nov. 7, 2000

(30) Foreign Application Priority Data

Nov. 10, 1999 (FR) .......................................... 99 14470

(51) Int. Cl.$^7$ ................................................. H04B 3/36
(52) U.S. Cl. ...................... 340/407.1; 381/70; 381/322; 434/114; 607/56; 607/145
(58) Field of Search ........................ 340/825.46, 825.19, 340/407.1; 434/114, 185, 156, 169; 704/207, 213; 381/322, 70; 607/56, 145

(56) References Cited

U.S. PATENT DOCUMENTS

| | | | |
|---|---|---|---|
| 4,250,637 A | | 2/1981 | Scott ........................... 434/114 |
| 4,685,448 A | * | 8/1987 | Shames et al. .............. 128/1 R |
| 5,012,520 A | * | 4/1991 | Steeger ......................... 381/68 |
| 5,035,242 A | | 7/1991 | Franklin et al. ......... 128/420.5 |
| 5,388,992 A | * | 2/1995 | Franklin et al. ............. 434/114 |
| 5,812,681 A | * | 9/1998 | Griffin .......................... 381/70 |
| 5,943,516 A | * | 8/1999 | Uchiyama et al. .......... 396/281 |

FOREIGN PATENT DOCUMENTS

| | | |
|---|---|---|
| DE | 33 22 108 | 12/1984 |
| DE | 38 34 442 | 11/1989 |
| EP | 0 184 332 A2 | 6/1986 |
| FR | 2577739 | 8/1986 |

* cited by examiner

Primary Examiner—Brent A. Swarthout
(74) Attorney, Agent, or Firm—Armstrong, Westerman, Hattori,LLP

(57) ABSTRACT

The tactile stimulation device designed to be used by a deaf person includes, in particular, an electroacoustic transducer. The invention is noteworthy in that the device consists of a case which can be held in one hand and which has a sensor associated with the electroacoustic transducer, which sensor is designed to enable turning the device on by touching said sensor.

26 Claims, 3 Drawing Sheets

TACTILE STIMULATION DEVICE FOR USE BY A DEAF PERSON

FILED OF THE INVENTION

The present invention concerns a tactile stimulation device capable of transforming an audio signal into vibrations which can be sensed by the skin of a person.

DESCRIPTION OF RELATED ART

The field of the invention is of special interest to deaf persons or to persons with a hearing deficiency whose auditory apparatus is deficient or nonfunctional.

In order for a deaf person to be able to understand a speaker, the most commonly known method consists in that this person learns to read lips.

There are, however, situations in which this person cannot see the speaker, for example, during operation of an intercom or when the person is attempting to respond at the end of a message from the speaker transmitted by an intercom.

There is also a real need to reinforce the capability of communication between a deaf person and a speaker during lip reading by helping the person perceive the vibrational differentiation of the various phonemes and also by enabling him to adjust his voice as a function of the ambient sound.

Attempts have been made to resolve this problem by proposing tactile stimulation devices including, generally, a microphone connected to a case including an electric current source as well as an electronic circuit board designed to convert the electrical signal provided by the microphone into an electrical signal designed to actuate an electroacoustic transducer.

An electroacoustic transducer is connected to the case and is held against the skin of the person, for example, by a bracelet putting the transducer into contact with the wrist of the person wishing to use it.

After learning a technique for recognition of the vibrations transmitted by the electroacoustic transducer to the skin of the person, the person is capable of interpreting the vibrations received by the skin and transmitted to the brain by the nerve endings of the skin, so as to understand the speech of the speaker.

However, this type of device does not give complete satisfaction because it is cumbersome, necessitates electrical links between its various components, and imposes the permanent wearing of a bracelet or of a device to affix the transducer on the skin.

Moreover, the human skin cannot sense vibrations whose frequency is greater than 1000 Hz.

BRIEF SUMMARY OF THE INVENTION

Whereas the human voice produces sounds whose highest frequencies for intelligibility are in the frequency band from 1000 to 3000 Hz, the same is true for the passband of intercoms and telephones which extends up to 3000 Hz.

Thus, it seemed interesting to be able to take advantage of the data of the human voice in the frequency band from 1000 to 3000 Hz to use them in the device of the invention.

The first object of the invention is thus to propose a tactile stimulation device of compact construction and extremely simple to implement.

Another object of the invention is to propose a tactile stimulation device which makes use of the data transmitted in the human voice, of which the frequency is between 1000 and 3000 Hz.

To that end, the device of the invention includes, in particular, an electroacoustic transducer and is characterized in that it is made up of a case which can be held in one hand and which has a sensor associated with the electroacoustic transducer, which sensor is designed to permit turning on the device by touching said sensor.

Thus, the device of the invention is compact and easy to actuate.

According to another characteristic of the invention, the sensor consists of an insulating support provided with conductive strips electrically isolated from each other and connected to the input of a contact detector.

According to another characteristic of the invention, each conductive strip is spiral-shaped and they are interlaced.

According to another characteristic of the invention, the sensor is pressed against the diaphragm of the electroacoustic transducer.

According to another characteristic of the invention, the device has a lowpass frequency filter which selects the frequencies below 800 Hz.

According to another characteristic of the invention, the device has a passband frequency filter connected to a frequency generator capable of modulating the signal received from said frequency filter in amplitude on a specified frequency.

According to another characteristic of the invention, the passband frequency filter selects the range of frequencies between 1000 Hz and 4000 Hz.

According to another characteristic of the invention, the operating frequency of the frequency generator is 900 Hz.

Thus, the high-pitched frequencies of the voice are transcribed by the device of the invention.

According to another characteristic of the invention, the power button of the device can assume a STOP position designed to cut the electric power to the device, an ON position, and a STANDBY position capable of turning on the device by means of the contact detector.

According to another characteristic of the invention, the device has an input connector provided to accommodate a removable microphone or a reception accessory T such as a magnetic loop receiver.

According to another characteristic of the invention, the device has an output connector provided to accommodate an external electroacoustic transducer.

According to another characteristic of the invention, the device has a control knob making it possible to use a potentiometer in order to modulate the intensity of the electric current supplying the electroacoustic transducer.

BRIEF DESCRIPTION OF THE DRAWINGS

The characteristics of the invention mentioned above, as well as others, will be understood more clearly upon reading the following description of an exemplary embodiment, with said description made in reference to the annexed figures, wherein.

DETAILED DESCRIPTION OF EMBODIMENTS OF THE INVENTION

Figure 1:
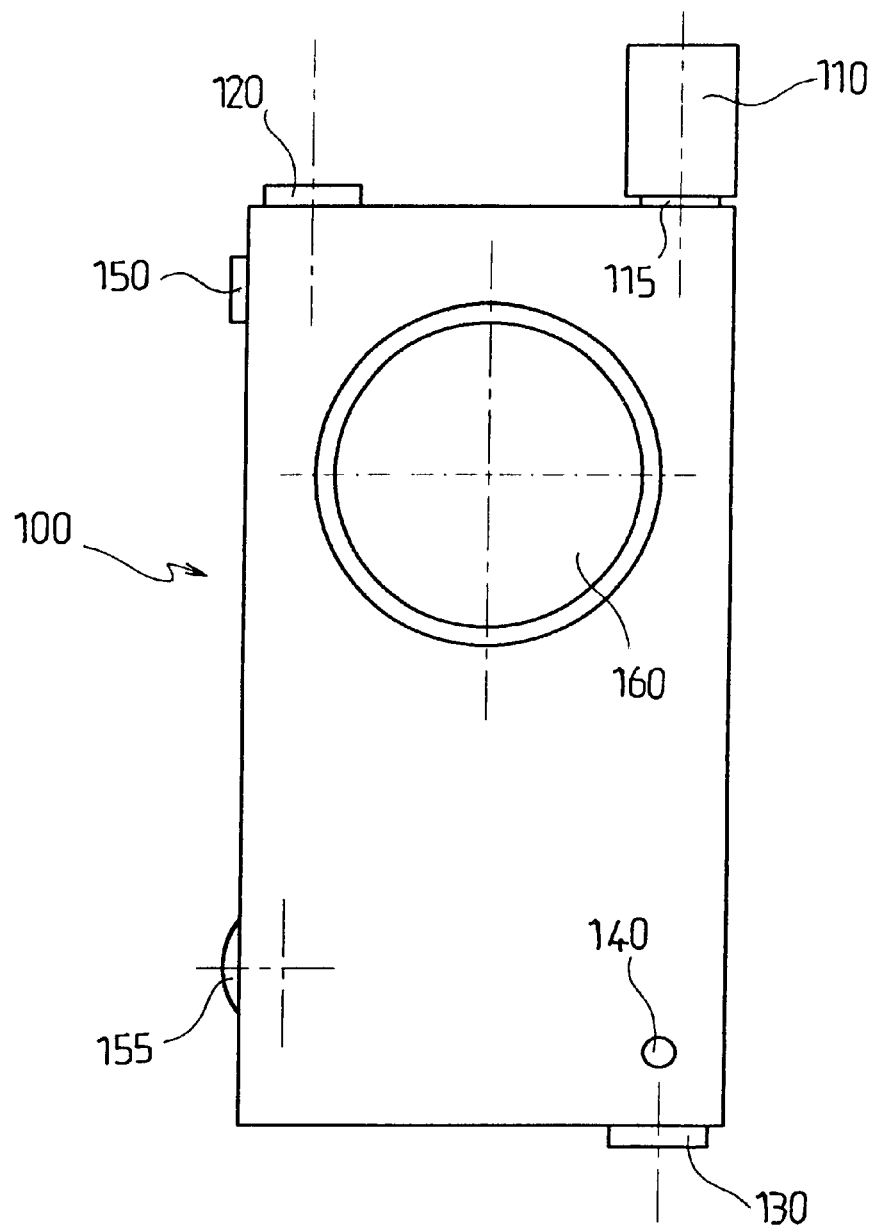
FIG. 1 depicts a front view of a tactile stimulation device according to the invention.

The tactile stimulation device depicted in FIG. 1 includes a parallelepiped-shaped case 100 which incorporates an electrical input connector 115 in which a removable microphone 110 is mounted.

The electrical input connector 115 can also be used to accommodate a receiving accessory such as a magnetic loop receiver replacing the removable microphone 110.

An electrical output connector 120 is provided in the case 100 to enable connection of another external electroacoustic transducer of the "integral" type, i.e., which enables capturing the vibrations in all the fingers which touch it on the front as well as on the back of said transducer.

An electrical power supply connector 130 is installed in the case 100. It enables external electrical powering of the device whose operation is signaled by an external power indicator light 140.

The case 100 of the stimulation device also incorporates a power button 150 of said device capable of assuming three positions: a STOP position to turn off the electrical power to the device, an ON position to turn on the device, and a STANDBY position which can turn on the device on demand as explained later in the description.

An electroacoustic transducer 160 is mounted on one of the main surfaces of the case 100.

A control knob 155 enables using a potentiometer to modulate the intensity of the electrical current to power the electroacoustic transducer 160.

Inside the case 100, an electrical power source, such as batteries or rechargeable batteries, is provided. These components are not shown.

Figure 2:
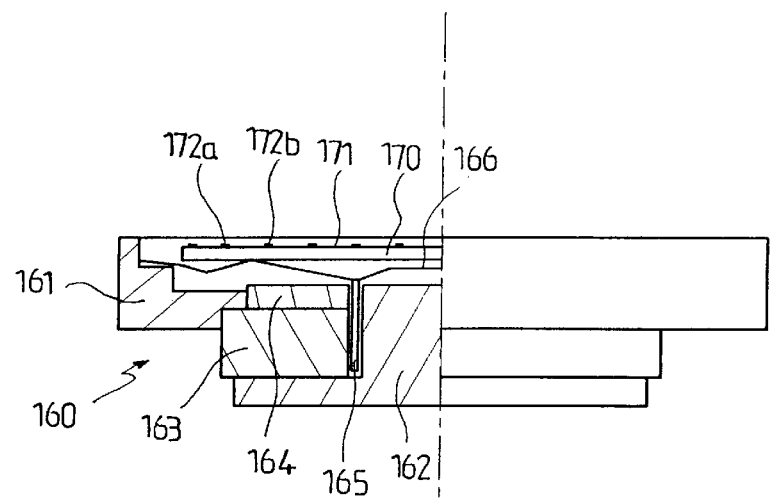
FIG. 2 depicts a sectional view of an electroacoustic transducer according to the invention.

In FIG. 2, the electroacoustic transducer 160 is made up in known fashion of a plastic housing 161 in which a magnetic motor, consisting of a steel base plate 162, a ring of a magnetic material 163, a steel ring 164, and a moving coil 165, is mounted concentrically.

A diaphragm 166 is attached, on the one hand, to the inside of the housing 161 and, on the other hand, to one end of the moving coil 165.

A sensor 170 is pressed against the diaphragm 166. It is designed to transmit the vibrations of the diaphragm 166 to one finger of the user, in particular to the thumb. It also serves to temporarily supply power to the device.

It is made up of an insulating support 171 of the printed circuit type of which the outside face is provided with conductive strips 172a and 172b made of copper disposed in a non-intersecting pattern and electrically isolated from each other.

Figure 3:
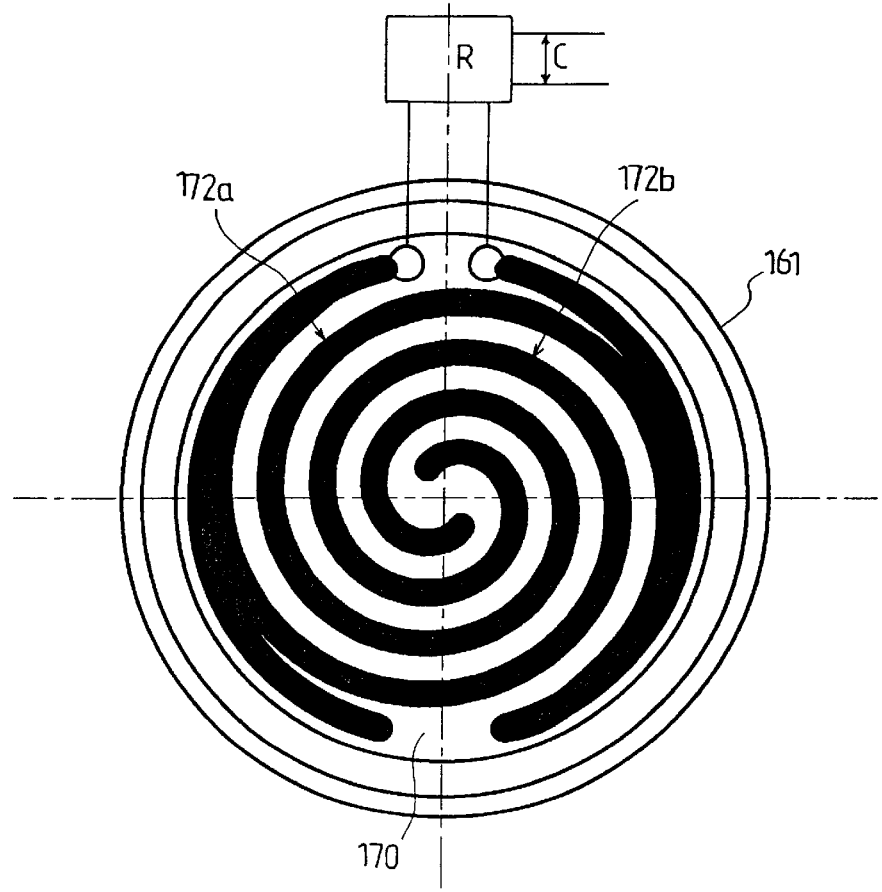
FIG. 3 depicts a top view of an electroacoustic transducer according to invention.

In a preferred embodiment, each of the conductive strips 172a and 172b forms a spiral, as is discernible in FIG. 3.

Each conductive strip 172a or 172b is connected to a contact detector.

The resistivity of the skin is used to actuate the contact detector R. The latter opens or closes an electrical contact C depending on whether or not tactile contact is made with the conductive strips 172a and 172b.

Figure 4:
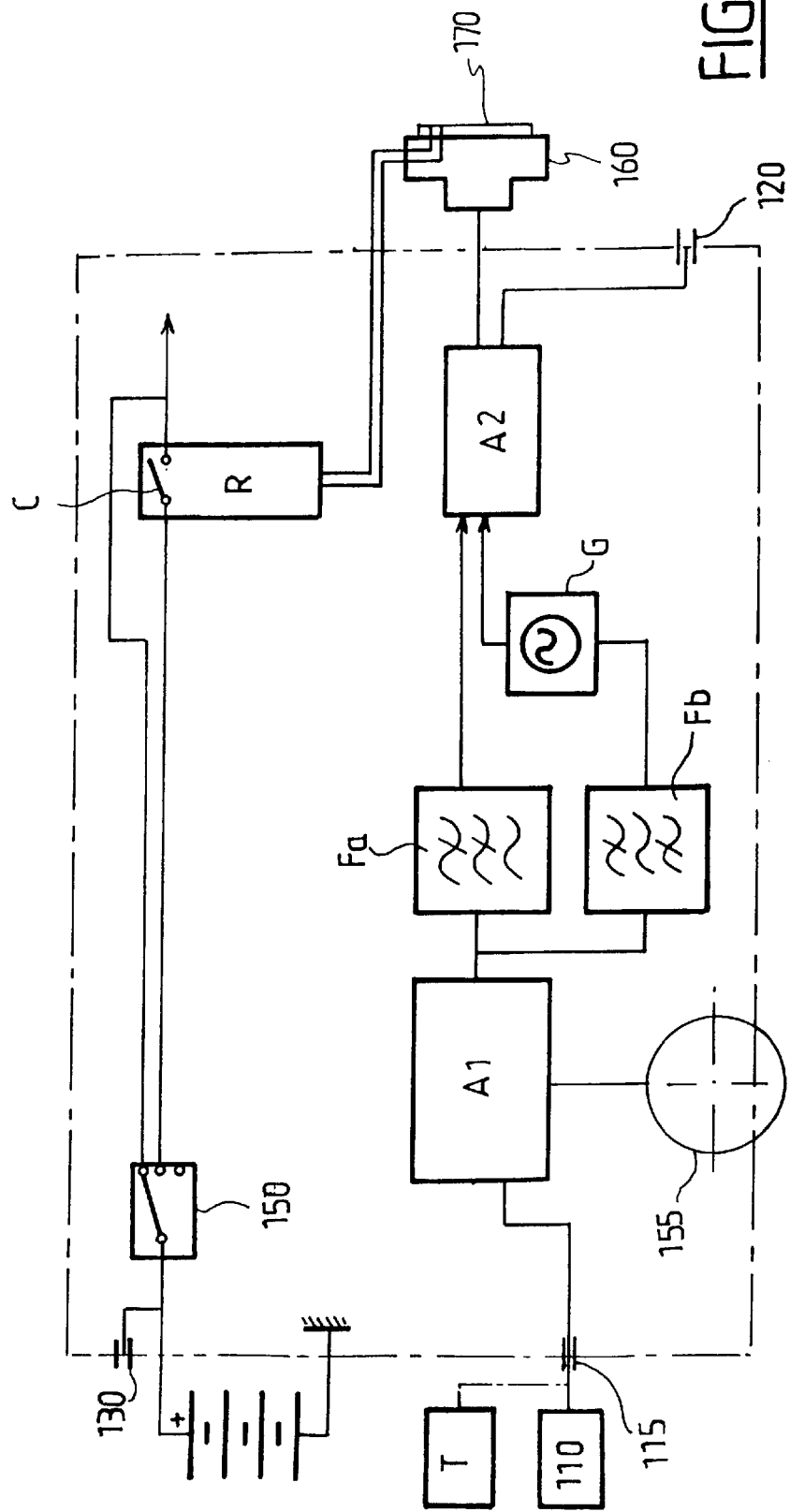
FIG. 4 depicts a schematic view of the operation of a tactile stimulation device according to the invention.

In FIG. 4, the schematic view of a tactile stimulation device according to the invention discloses its major functions.

The components mounted on the printed circuit are depicted inside a rectangular box shown by a light dot-dash line.

The voice of a speaker is picked up by the removable microphone 110 or by a receiving accessory T such as a magnetic loop receiver, mounted in the electrical input connector 115.

The magnetic loop receiver uses a magnetic field produced by a magnetic loop.

Magnetic loops are used in certain conference rooms and enable the transmission of the voice of the lecturer or of a translation of his speech, by magnetic coupling with receivers with which the listeners are equipped.

Then, the signal produced by the removable microphone 110 or by a receiving accessory T is transmitted to a first amplifier A1.

The signal is next transmitted in parallel to two frequency filters Fa and Fb. The first lowpass filter Fa selects frequencies up to 800 Hz; then, the filtered signal is transmitted to a first input of the second power amplifier A2.

The second passband filter Fb selects the frequencies between 1000 Hz and 4000 Hz and then supplies the filtered signal to a frequency generator G which modulates the amplitude of the signal to a frequency of 900 Hz.

The signal produced by the frequency generator G is then introduced into a second input of the amplifier A2.

The signal produced by the amplifier A2 is used to actuate the electroacoustic transducer 160.

Thus, the high-pitched frequencies produced by the human voice such as the sibilants "CHE", which are of significance for the comprehension of the human voice by a deaf person, are made perceptible by the device of the invention.

The signal produced by the amplifier A2 is also delivered to the electrical output connector 120.

Other types of electroacoustic transducers may be connected to the electrical output connector 120, such as an external electroacoustic transducer designed to be used between the fingers of the person.

The contact detector R connected to the sensor 170 of the electroacoustic transducer 160 is mounted in series with the ON button 150 when it is switched to the STANDBY position. When a person wishes to use the tactile stimulation device to understand the voice of a speaker, he takes the device in one hand, possibly turns it on, or to the STANDBY position with the power button 150.

If the device is ON, the person points the device, as necessary, such that the removable microphone 110 is oriented in the direction from which the voice is coming.

The person makes thumb contact with the sensor 170 in order to sense and to interpret the vibrations output by the electroacoustic transducer 160.

If the device is in the STANDBY position, the contact of the user's thumb with the conductive strips 172a and 172b of the sensor 170 induces non-zero electrical resistance between the conductive strips 172a and 172b. The magnitude of this electrical resistance is picked up by the contact detector R which closes the electrical contact C and turns the device on.

The person can then sense and interpret the vibrations output by said electroacoustic transducer 160.

The control knob 155 may be used to modulate the power delivered by the electroacoustic transducer 160 to adapt the device to the sensory conditions of the person using it.

The tactile stimulation device of the invention makes it possible to transform the sounds emitted by the voice of a person into tactile vibrations which can be sensed by the skin of a person, especially a finger tip, which is a skin zone with a particularly large number of nerves and is sensitive to the specific perception of the sense of touch.

The tactile stimulation device of the invention has a compact construction, which permits carrying it in a pocket.

All its components are integrated into a single case.

No preparation whatsoever is necessary to initiate its use to detect voices and ambient sound.

This device can thus be used immediately by a deaf person during the most common everyday situations, such as when the person must respond to an intercom or when he must speak to someone on the street.

The data transmitted in the form of tactile vibrations to the person who uses it cover certain frequency bands carried by the human voice and filter certain interfering frequencies.

The use of the tactile stimulation device of the invention is also conceivable for training in vibrotactile comprehension of the phonemes in lip reading.

The tactile stimulation device of the invention can also be used by a deaf person for him to learn to control his voice.

The tactile stimulation device of the invention also enables its user to assess the level of ambient noise in order to adjust his own voice.

In a variant with a simplified design, the filters fa and fb as well as the frequency generator g are not provided in the device of the invention.

What is claimed is:

1. Tactile stimulation device designed to be used by a deaf person comprising
    a case which can be held in one hand,
    a sensor associated with an electroacoustic transducer, and
    an input connector provided to accommodate a removable microphone or a receiving accessory,
    said sensor, said transducer, and said input connector being mounted on said case,
    said transducer producing a vibration output (i) representing ambient sounds collected by the microphone or receiving accessory and (ii) capable of being sensed by a finger,
    said sensor being designed to enable turning the device on by touching said sensor, such that the device has a compact construction making it possible to carry the device in a pocket, taking the device in one hand, turning the device on, and sensing the vibration output of the transducer with a finger.

2. Device according to claim 1, wherein the sensor consists of an insulating support provided with conductive strips electrically isolated from each other and connected to the input of a contact detector.

3. Device according to claim 2, wherein the conductive strips each have the shape of a spiral and are interlaced.

4. Device according to claim 1, wherein the sensor is pressed against a diaphragm of the electroacoustic transducer.

5. Device according to claim 2, wherein the sensor is pressed against a diaphragm of the electroacoustic transducer.

6. Device according to claim 3, wherein the sensor is pressed against a diaphragm of the electroacoustic transducer.

7. Device according to claim 1, which includes a lowpass frequency filter which selects the frequencies lower than 800 Hz.

8. Device according to claim 2, which includes a lowpass frequency filter which selects the frequencies lower than 800 Hz.

9. Device according to claim 1, which includes a passband frequency filter connected to a frequency generator capable of modulating the signal received from, said frequency filter in amplitude to a specified frequency.

10. Device according to claim 2, which includes a passband frequency filter connected to a frequency generator capable of modulating the signal received from said frequency filter in amplitude to a specified frequency.

11. Device according to claim 9, wherein the passband frequency filter selects the range of frequencies between 1000 Hz and 4000 Hz.

12. Device according to claim 10, wherein the passband frequency filter selects the range of frequencies between 1000 Hz and 4000 Hz.

13. Device according to claim 9, wherein the operating frequency of the frequency generator is 900 Hz.

14. Device according to claim 10, wherein the operating frequency of the frequency generator is 900 Hz.

15. Device according to claim 11, wherein the operating frequency of the frequency generator is 900 Hz.

16. Device according to claim 12, wherein the operating frequency of the frequency generator is 900 Hz.

17. Device according to claim 1, including a power button, wherein the power button may assume a STOP position designed to cut the power supply of the device, an ON position of the device, and a STANDBY position capable of starting the device by using a contact detector.

18. Device according to claim 1, wherein the input connector accommodates a receiving accessory which is a magnetic loop receiver.

19. Device according to claim 1, which includes an output connector provided to accommodate an external electroacoustic transducer.

20. Device according to claim 1, which includes a control knob enabling use of a potentiometer to modulate the intensity of the electrical current to power the electroacoustic transducer.

21. Tactile stimulation device designed to be used by a deaf person comprising a case which can be held in one hand and a sensor associated with an electroacoustic transducer, said sensor being designed to enable turning the device on by touching said sensor, wherein the sensor consists of an insulating support provided with conductive strips electrically isolated from each other and connected to the input of a contact detector, and wherein the conductive strips each have the shape of a spiral and are interlaced.

22. Device according to claim 21, wherein the sensor is pressed against the diaphragm of the electroacoustic transducer.

23. Tactile stimulation device designed to be used by a deaf person comprising a case which can be held in one hand and a sensor associated with an electroacoustic transducer, said sensor being designed to enable turning the device on by touching said sensor, including a power button, wherein the power button may assume a STOP position designed to cut the power supply of the device, an ON position of the device, and a STANDBY position capable of starting the device by using a contact detector.

24. Tactile stimulation device designed to be used by a deaf person comprising a case which can be held in one hand and a sensor associated with an electroacoustic transducer, said sensor being designed to enable turning the device on by touching said sensor, which includes an input connector provided to accommodate a receiving accessory, wherein the receiving accessory is a magnetic loop receiver.

25. Tactile stimulation device designed to be used by a deaf person comprising a case which can be held in one hand and a sensor associated with an electroacoustic transducer,
    an input connector provided to accommodate a removable microphone or a receiving accessory,
    said transducer producing a vibration output (I) representing ambient sounds collected by the microphone or receiving accessory and (ii) capable of being sensed by a finger, said sensor being designed to enable turning the device on by touching said sensor, wherein the sensor is pressed against the diaphragm of the electroacoustic transducer.

26. Tactile stimulation device designed to be used by a deaf person comprising a case which can be held in one hand, a sensor associated with an electroacoustic transducer, and an input connector provided to accommodate a removable microphone or a receiving accessory, said transducer producing a vibration output (i) representing ambient sounds collected by the microphone or receiving accessory and (ii) capable of being sensed by a finger, said sensor being designed to enable turning the device on by touching said sensor, wherein all components of the tactile stimulation device are integrated into the case.

* * * * *